(12) United States Patent
Nishiyama

(10) Patent No.: US 7,923,700 B2
(45) Date of Patent: Apr. 12, 2011

(54) SAMPLE INSPECTION APPARATUS, SAMPLE INSPECTION METHOD AND SAMPLE INSPECTION SYSTEM

(75) Inventor: Hidetoshi Nishiyama, Tokyo (JP)

(73) Assignee: JEOL Ltd., Tokyo (JP)

( * ) Notice: Subject to any disclaimer, the term of this patent is extended or adjusted under 35 U.S.C. 154(b) by 680 days.

(21) Appl. No.: 11/960,267

(22) Filed: Dec. 19, 2007

(65) Prior Publication Data
US 2010/0096549 A1 Apr. 22, 2010

(30) Foreign Application Priority Data

Dec. 19, 2006 (JP) ................................. 2006-340682
Jan. 23, 2007 (JP) ................................. 2007-012414

(51) Int. Cl.
*H01J 37/20* (2006.01)
(52) U.S. Cl. ................... 250/440.11; 250/310; 250/309; 250/441.11
(58) Field of Classification Search .................. 250/310, 250/309, 440.11, 441.11
See application file for complete search history.

(56) References Cited

U.S. PATENT DOCUMENTS

| | | | | |
|---|---|---|---|---|
| 5,312,519 A * | 5/1994 | Sakai et al. | .................... | 134/1.1 |
| 7,745,802 B2 * | 6/2010 | Nishiyama et al. | ...... | 250/442.11 |
| 2004/0046120 A1 * | 3/2004 | Moses et al. | ................... | 250/311 |
| 2005/0173632 A1 * | 8/2005 | Behar et al. | .................... | 250/311 |
| 2009/0242762 A1 * | 10/2009 | Nishiyama et al. | ........... | 250/307 |
| 2009/0250609 A1 * | 10/2009 | Nishiyama et al. | ........... | 250/306 |
| 2009/0314955 A1 * | 12/2009 | Nishiyama et al. | ...... | 250/442.11 |
| 2010/0051803 A1 * | 3/2010 | Koizumi et al. | .............. | 250/306 |

FOREIGN PATENT DOCUMENTS

| | | |
|---|---|---|
| JP | 06-318445 | 11/1994 |
| JP | 2004-515049 | 5/2004 |

OTHER PUBLICATIONS

Green, Evan Drake Harriman, Chapter 1. Introduction, Atmospheric Scanning Electron Microscopy, Stannford University, 1992, pp. 1-12.

* cited by examiner

*Primary Examiner* — Jack I Berman
(74) *Attorney, Agent, or Firm* — The Webb Law Firm

(57) ABSTRACT

Sample inspection apparatus, sample inspection method, and sample inspection system are offered which can give a stimulus to a sample held on a film when the sample is inspected by irradiating it with a primary beam (e.g., an electron beam or other charged-particle beam) via the film. The apparatus has the film, a vacuum chamber, primary beam irradiation column, signal detector, and a controller for controlling the operations of the beam irradiation column and signal detector. The sample is held on a first surface of the film opened to permit access to the film. The vacuum chamber reduces the pressure of the ambient in contact with a second surface of the film. The irradiation column irradiates the sample with the primary beam via the film from the second surface side. The detector detects a secondary signal produced from the sample in response to the irradiation.

25 Claims, 3 Drawing Sheets

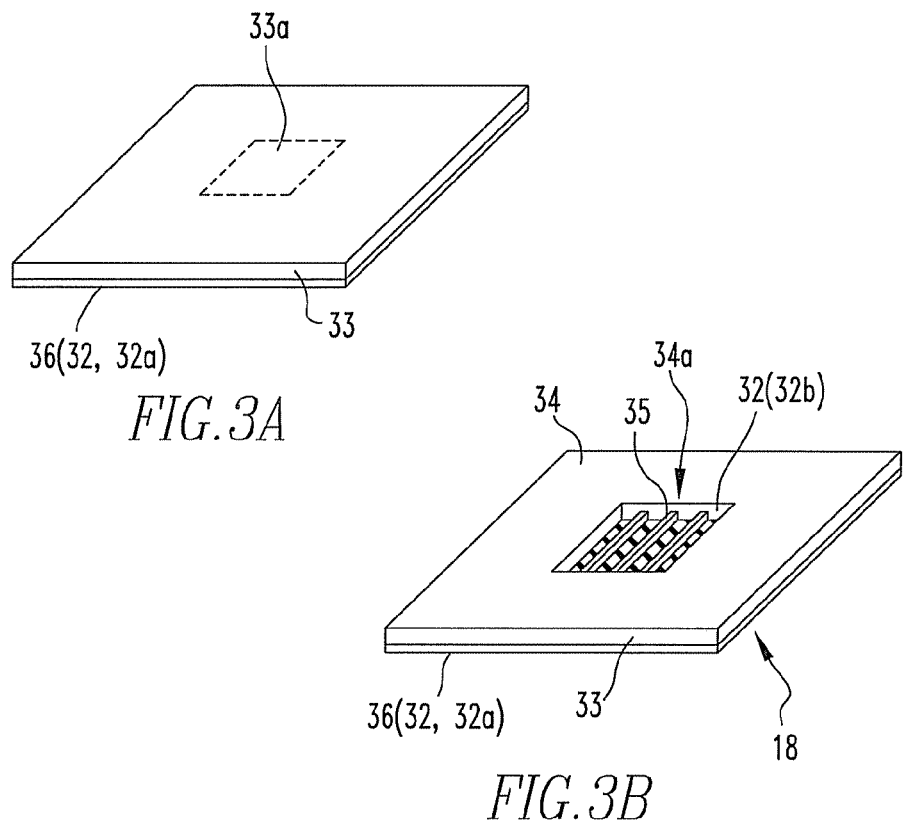
FIG.3A
FIG.3B
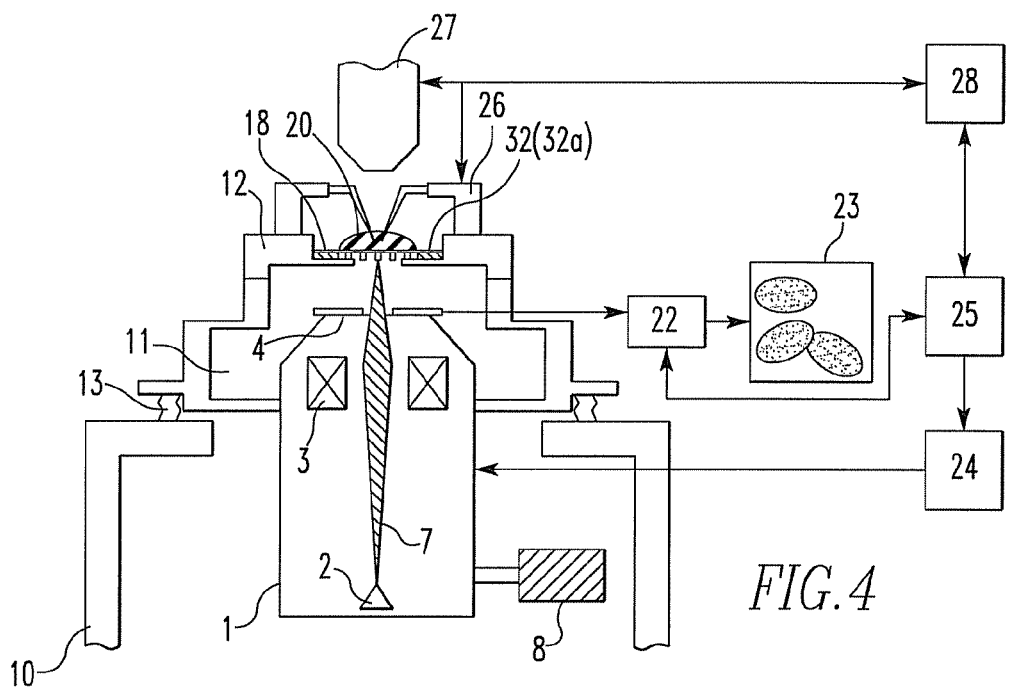
FIG.4

SAMPLE INSPECTION APPARATUS, SAMPLE INSPECTION METHOD AND SAMPLE INSPECTION SYSTEM

BACKGROUND OF THE INVENTION

1. Field of the Invention

The present invention relates to a sample inspection apparatus, sample inspection method, and sample inspection system capable of inspecting a sample by irradiating the sample held on a film with a primary beam, such as a charged-particle beam. Especially, the present invention relates to techniques permitting one to observe reactions of a sample consisting of biological cells when a stimulus is given to the cells and to inspect the sample.

2. Description of Related Art

In life science and pharmaceutical applications, it is important that stimuli (such as electricity, chemical substances, and medicines) are given to biological cells and that resulting reactions are observed. In the past, optical microscopes have been used for such observations. Often, important parts to be observed are microscopic regions of less than 0.1 µm, which cannot be observed with optical microscopes.

For example, diseases arising from inability to exchange intercellular messengers (signaling molecules) among biological cells normally include hypertension, diabetes insipidus, arrhythmia, muscular disorders, diabetes, and depression. Exchange of these substances among cells is performed by membrane protein molecules, such as receptors and ion channels having sizes of about 10 nm and existing in cell membranes. Because it is difficult to observe such membrane protein molecules with optical microscopes, there has been a demand for a technique enabling observation using a scanning electron microscope (SEM) with high resolution.

However, a sample to be inspected with an inspection apparatus incorporating SEM capabilities is normally placed in a sample chamber whose inside pressure has been reduced by vacuum pumping. The sample placed in the sample chamber which, in turn, is placed in a reduced-pressure ambient in this way is irradiated with an electron beam (charged-particle beam). Secondary signals, such as secondary electrons or backscattered electrons, produced from the sample in response to the irradiation are detected.

In such inspection of a sample using SEM, the sample is exposed to a reduced-pressure ambient. Therefore, moisture evaporates from the sample, so that the cells die. This makes it impossible to observe reactions to stimuli.

Accordingly, when an inspection is performed under the condition where the sample contains moisture, it is necessary to prevent the sample from being exposed to the reduced-pressure ambient; otherwise, moisture would evaporate from the sample. One conceivable method of inspecting a sample using SEM without exposing the sample to a reduced-pressure ambient in this way consists of preparing a sample holder whose opening (aperture) has been sealed off by a film, placing the sample in the holder, and installing the holder in an SEM sample chamber that is placed in the reduced-pressure chamber.

The inside of the sample holder in which the sample is placed is not evacuated. The film that covers the opening formed in the sample holder can withstand the pressure difference between the reduced-pressure ambient inside the SEM sample chamber and the ambient (e.g., atmospheric-pressure ambient) of the inside of the sample holder that is not pumped down. Furthermore, the film permits an electron beam to pass therethrough (see JP-T-2004-515049).

When a sample is inspected, an electron beam is directed at the sample placed within the sample holder from outside the sample holder via the film on the sample holder placed in the SEM sample chamber that is in the reduced-pressure ambient. Backscattered electrons are produced from the irradiated sample. The backscattered electrons pass through the film on the sample holder and are detected by a backscattered electron detector mounted in the SEM sample chamber. Consequently, an SEM image is derived. However, with this technique, the sample is sealed in the closed space and so it has been impossible to give a stimulus to cells using a manipulator.

An example of a method of obtaining an SEM image by irradiating a sample with an electron beam via a film capable of withstanding the pressure difference between a vacuum and atmospheric pressure and detecting backscattered electrons emanating from the sample in this way is described also in Atmospheric Scanning Electron Microscopy, Green, Evan Drake Harriman, Ph. D., Stanford University, 1993 (especially Chapter 1: Introduction).

An example of a method of obtaining an image using a transmission electron microscope by placing a pair of films of the structure described above in an opposite relation to each other and placing the sample between the films is described in JP-A-47-24961 and JP-A-6-318445. Especially, JP-A-47-24961 makes a mention of a method of using such a pair of films. That is, an SEM image of a sample placed between the films is derived.

Morphological variations based on reactions of cells after a stimulus is given to the cells using a manipulator take place in microscopic regions within the cells. Therefore, the variations cannot be observed with an optical microscope. Hence, observation using SEM is essential. In order to observe the cells by SEM while maintaining the liquid, the sample (cells) is sealed in a sample holder. An electron beam is directed at the sample via a film formed on the sample holder, thus obtaining an image. However, with the aforementioned sample holder, the inside of the holder is a closed space. Consequently, it has been impossible to use a manipulator for giving a stimulus.

SUMMARY OF THE INVENTION

It is an object of the present invention to provide a sample inspection apparatus, sample inspection method, and sample inspection system in which a sample held on a film is irradiated with a primary beam, such as a charged-particle beam (e.g., an electron beam), such that the beam hits the sample via the film. Consequently, a stimulus can be given to the sample held on the film when the sample is inspected.

When a stimulus is given to a sample consisting of biological cells with a manipulator, portions where variations take place are mainly vicinities of the portions to which the stimulus was given. It is important to place these regions within the field of view of the SEM image quickly in order to reduce radiation damage to the cells and to achieve ease of use. Consequently, this is another object of the present invention.

A further object of the present invention lies when (i) a sample holder that is opened to permit a stimulus to be given to such a sample with a manipulator is used, (ii) the sample can be irradiated with an electron beam via a film formed on the sample holder to thereby permit SEM imaging, and (iii) the manipulator disposed on the open side is allowed to give a stimulus to the sample.

For example, if the tip of the manipulator touches the film on the sample holder, and if an unwanted external force is applied to the film from the tip of the manipulator, the film will be damaged. As a result, if the film is destroyed, the sample on the film leaks into the SEM instrument during SEM imaging and diffuses. Consequently, the instrument is contaminated.

It is an additional object of the present invention to provide a sample inspection apparatus, sample inspection method, and sample inspection system in which a sample is prevented from being damaged by a manipulator when the sample is inspected by giving a stimulus to the sample by the manipulator and irradiating the sample with a primary beam via a film.

It is yet another object of the present invention to provide a sample inspection apparatus, sample inspection method, and sample inspection system in which contamination of the inside of an SEM vacuum chamber can be prevented during observation of a sample.

A first sample inspection apparatus, according to the present invention, has: a film having a first surface on which a sample is held such that the first surface is opened to permit access to the sample; a vacuum chamber for reducing the pressure of an ambient in contact with a second surface of the film; primary beam irradiation system for irradiating the sample via the film with a primary beam from a side of a second surface of the film; signal detector for detecting a secondary signal produced from the sample in response to the irradiation; overall controller for controlling operations of the primary beam irradiation system and signal detector.

A second sample inspection apparatus, according to the present invention, has: a film having a first surface on which a sample is held; a vacuum chamber for reducing the pressure of an ambient in contact with a second surface of the film; primary beam irradiation system connected with the vacuum chamber and irradiating the sample with a primary beam via the film; and signal detector for detecting a secondary signal produced from the sample in response to the beam irradiation. The sample inspection apparatus further includes: optical image acquisition system for acquiring an optical image of the sample; and overall controller for controlling operations of the primary beam irradiation system, signal detector, and optical image acquisition system.

A first sample inspection method, according to the present invention, is implemented to inspect a sample using the sample inspection apparatus.

A second sample inspection method, according to the present invention, starts with preparing a sample held on a first surface of a film such that the first surface is opened to permit access to the sample. The sample is irradiated via the film with a primary beam from a side of a second surface of the film that is in contact with a reduced-pressure ambient. A secondary signal produced from the sample in response to the irradiation is detected. Thus, information about the sample is obtained.

A third sample inspection method, according to the present invention, starts with irradiating a sample with a primary beam from a primary beam irradiation system via a film. Information (first information) about the sample is obtained based on the results of the irradiation. A physical, electrical, or chemical action is applied to the sample. Then, the sample is irradiated with the primary beam via the film. Information (second information) about the sample is obtained based on the irradiation. The first information is compared with the second information.

A sample inspection system, according to the present invention, has an information processor as well as the aforementioned sample inspection apparatus. The information processor makes a decision on the sample from information derived based on a secondary signal from the sample, the secondary signal being detected by the sample inspection apparatus.

In the present invention, a sample is irradiated with a primary beam via a film. A secondary signal produced from the sample in response to the beam irradiation can be detected. The sample is held on a first surface of the sample such that the first surface is opened to permit a manipulator or the like to access to the film. Therefore, the sample can be manipulated by the manipulator. In consequence, a stimulus can be given to the sample held on the sample by the manipulator.

At this time, SEM imaging is enabled while preventing evaporation of liquid surrounding the sample by placing the sample in a normal-pressure ambient (atmospheric-pressure ambient). A stimulus can be given to the sample using the manipulator. The resulting reactions can be observed.

The dose of the primary beam hitting the film or sample can be reduced to a minimum by restricting the range irradiated with the primary beam to surroundings of the portion of the sample to which the stimulus has been given by the manipulator, using positional information about the manipulator. Consequently, beam damage to the film or sample can be reduced.

Furthermore, in the present invention, the sample is irradiated with the primary beam via the film. A secondary signal produced from the sample in response to the beam irradiation can be detected. An optical image of the sample can be acquired by the optical image acquisition system.

Even when the film is destroyed by the manipulator, contamination of the inside of the instrument can be prevented by mounting an open-close valve for partitioning off the space between the film and the primary beam irradiation system.

In addition, in the present invention, the operation of the manipulator is controlled based on the result of a measurement of the position of the film or on the result of a measurement of an electrical or physical amount between the tip of the manipulator and the film to prevent the tip of the manipulator from touching the film or to limit the operation of the manipulator when the tip is in contact with the film.

Consequently, the tip of the manipulator can be prevented from touching the film or, if the tip touches the film, application of an unwanted external force to the film by the tip of the manipulator can be prevented. This assures that damage to the film due to operation of the manipulator can be prevented.

As a result, when the sample on the film is observed or inspected using SEM, it is assured that destruction of the film due to the manipulator is prevented; otherwise, the sample would diffuse, contaminating the apparatus.

The provision of the open-close valve described above makes it possible to partition off the space between the film and the primary beam irradiation system when or immediately before the tip of the manipulator touches the film. Therefore, if the film should be destroyed, contamination of the apparatus can be prevented.

These and other objects and advantages of the present invention will become more apparent as the following description proceeds.

BRIEF DESCRIPTION OF THE DRAWINGS

FIGS. 3A and 3B illustrate a method of creating a sample holder for use in the present invention;

FIG. 4 is a schematic diagram showing a second embodiment of the sample inspection apparatus according to the present invention;

DESCRIPTION OF THE PREFERRED EMBODIMENTS

Embodiments of the present invention are hereinafter described with reference to the drawings.

Embodiment 1

Figure 1:
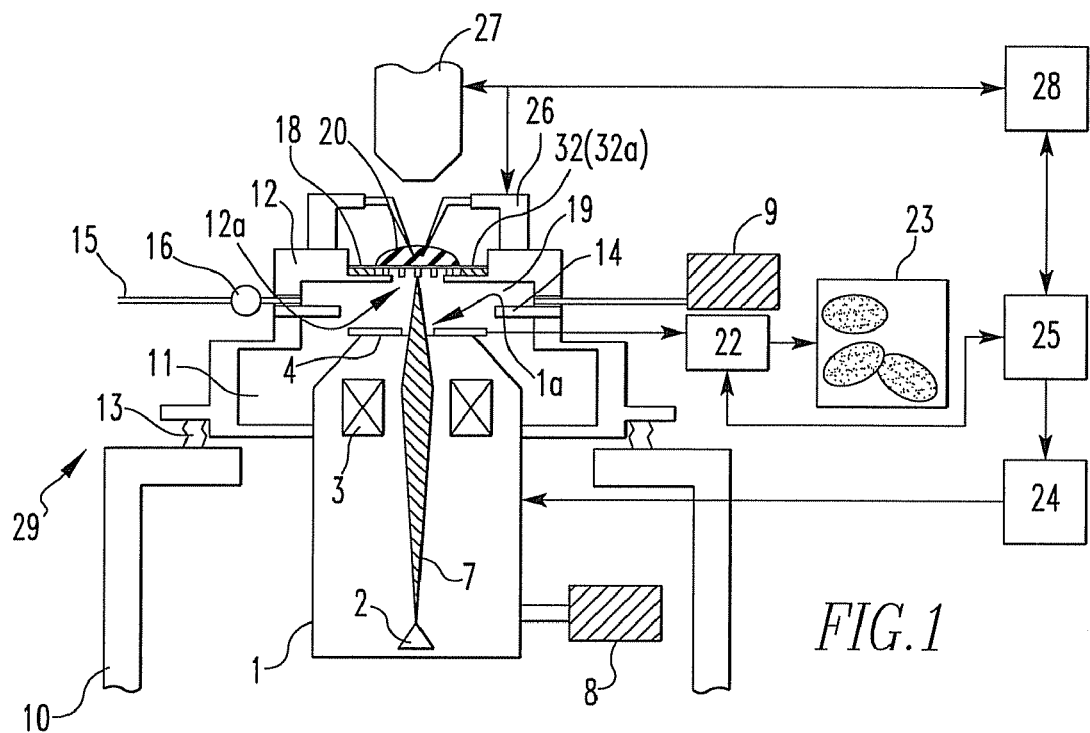
FIG. 1 is a schematic diagram showing a first embodiment of the sample inspection apparatus according to the present invention.

FIG. 1 is a schematic diagram showing a first embodiment of an inspection apparatus according to the present invention. In the figure, an electron gun 2 forming an electron source is disposed in an electron optical column 1 forming primary beam irradiation system. An electron beam (a kind of charged-particle beam) 7 acting as a primary beam is emitted from the electron gun 2 and accelerated. The beam 7 is focused by a condenser lens (objective lens) 3.

The electron beam 7 focused in this way is made to hit a sample 20 via a sample-holding film 32. The sample 20 is held on this sample-holding film 32 forming a sample holder 18. At this time, the beam 7 is deflected by deflection system (not shown). As a result, the beam 7 scans the sample 20. The front end of the electron optical column 1 is connected with a vacuum chamber 11. The base end of the electron optical column 1 in which the electron gun 2 is mounted is located below the vacuum chamber 11. The sample 20 is held on the upper surface, or first surface, 32a of the sample-holding film 32. The ambient in contact with the lower surface, or second surface, of the film 32 is reduced in pressure by the vacuum chamber 11. As can be seen from FIG. 1, the upper surface 32a of the film 32 is opened.

The electron beam 7 released from the electron gun 2 travels upward through the electron optical column 1 and passes through the space inside the vacuum chamber 11 by way of an opening 1a formed at the front end of the column 1 and then through the film 32. Then, the beam reaches the sample 20. In this way, the electron optical column 1 forms the primary beam irradiation system. In the present embodiment, the column is an inverted electron optical column. A backscattered electron detector 4 forming signal detection means is mounted inside the vacuum chamber 11 and near the front end of the column 1. For example, a semiconductor detector utilizing a PN junction or a scintillator detector utilizing a YAG crystal is used as the backscattered electron detector 4.

The inside of the electron optical column 1 is evacuated to a desired pressure (e.g., $10^{-4}$ to $10^{-5}$ Pa) by vacuum pump 8. Furthermore, the inside of the vacuum chamber 11 is evacuated to a desired pressure (e.g., $10^{-3}$ to $10^{-4}$ Pa) by a vacuum pump (not shown). The vacuum chamber 11 is placed over a pedestal 10 via a vibration-proofing device 13.

A sample holder placement portion 12 is formed on top of the vacuum chamber 11 and provided with a hole 12a to permit passage of the electron beam 7. The sample holder 18 is placed on the placement portion 12 via an O-ring (not shown). Consequently, the sample holder 18 is withdrawably supported in the vacuum chamber 11. When the inside of the vacuum chamber 11 is in a vacuum state, the sample holder can be moved horizontally a distance, if the distance is only about 0.5 mm. The position of the sample 20 relative to an optical microscope image or SEM image can be adjusted.

Figure 2:
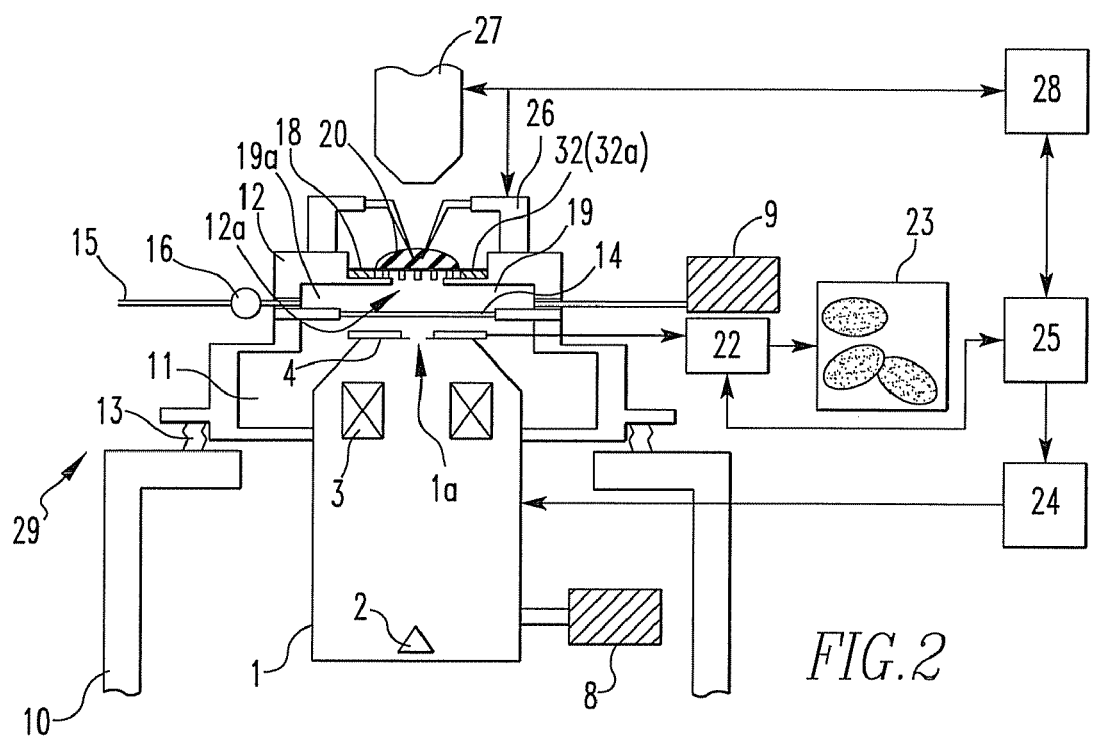
FIG. 2 is a schematic diagram showing the first embodiment of the sample inspection apparatus according to the present invention.

An open-close valve 14 is mounted in the vacuum chamber 11 near its top portion and used to partition off the space 19 between the sample-holding film 32 of the sample holder 18 and the front end of the electron optical column 1 (primary beam irradiation system) within the vacuum chamber 11. In FIG. 1, the open-close valve 14 is opened. When the valve 14 is closed, the space 19 is partitioned off in the vacuum chamber 11 as shown in FIG. 2.

When the space 19 is partitioned off by the open-close valve 14 in this way, a closed space 19a is formed between the valve 14 and the sample-holding film 32. The closed space 19a is partitioned by the valve 14 on its one side and located on the side of the sample holder 18.

A vacuum pump 9 is in communication with the closed space 19a. The vacuum pump 9 can evacuate the closed space 19a independently. A gas supply (not shown) is connected with the closed space 19a and supplies a gas, such as nitrogen, or air into the closed space 19a to return the closed space 19a from a pressure-reduced state to normal-pressure (atmospheric-pressure) state. In consequence, the closed space 19a can be returned from the reduced-pressure state to the normal-pressure state independently.

A cleaning dispenser (not shown) is connected with the closed space 19a to supply a cleaning agent into the closed space 19a, for cleaning it. As a result, the wall surface of the closed space 19a is cleaned.

The used cleaning agent is a cleaning fluid consisting of at least one of a detergent, ethanol, alcohol, acetone, and aqueous hydrogen peroxide. Alternatively, vapors of these materials may be used. The cleaning agent supplied in the closed space 19a is discharged from it through a discharge tube 15 after the cleaning. An open-close valve 16 is mounted in the discharge tube 15. The open-close valve 16 is opened to permit the cleaning agent to be discharged to the outside through the discharge tube 15. When inspection (described later) of the sample is carried out, the valve 16 is closed.

The closed space 19a can be disinfected without using the cleaning agent by irradiating the closed space 19a with ultraviolet radiation.

As shown in FIG. 3B, the sample holder 18 has the sample-holding film 32. The first surface 32a (the lower surface in FIG. 3B; in FIG. 1, the upper surface) of the film 32 is exposed. The sample 20 containing liquid is supplied onto the first surface 32a of the sample-holding film 32. Since the first surface 32a is under atmospheric pressure (in an atmospheric-pressure ambient), evaporation of the moisture can be suppressed to a minimum. The sample holder 18 includes a body 34 on the second surface 32b (the upper surface in FIG. 3B; in FIG. 1, the lower surface) of the sample-holding film 32.

The body 34 is centrally provided with an opening 34a. A central portion of the second surface 32b of the sample-holding film 32 is exposed to the inside ambient of the vacuum chamber 11 through the opening 34a. The first surface 32a of the sample-holding film 32 is exposed to the atmospheric-pressure ambient, while the second surface 32b is exposed to the vacuum ambient. In order to withstand the pressure difference, the film 32 is reinforced with a lattice 35 if necessary.

A method of creating the sample holder 18 is next described. First, as shown in FIG. 3A, a substrate having a silicon layer 33 and a silicon nitride film 36 formed on one surface (the lower surface in the figure) of the silicon layer 33 is prepared. At this time, the first surface (in the figure, the lower surface) of the silicon nitride film 36 is exposed. The second surface of the silicon nitride film 36 is covered with the silicon layer 33. The silicon layer 33 forms the body 34 of the sample holder 18. The silicon nitride film 36 forms the sample-holding film 32 of the sample holder 18.

Then, a central portion 33*a* of the other surface (upper surface) of the silicon layer 33 in FIG. 3A is selectively etched. As a result, the opening 34*a* is formed in the central portion 33*a* of the silicon layer 33 as shown in FIG. 3B. Consequently, parts of the second surface of the silicon nitride film 36 are exposed through the opening 34*a*. At this time, to reinforce the silicon nitride film 36, lattice 35 comprising plural pillars of silicon are left in the opening 34*a*. Where the silicon nitride film 36 has sufficient strength, the lattice 35 is not necessary.

In the opening 34*a*, the second surface of the silicon nitride film 36 is exposed through the portions where the pillars are not present. The silicon nitride film 36 forms the sample-holding film 32 of the sample holder 18. The second surface of the silicon nitride film 36 corresponds to the second surface 32*b* of the sample-holding film 32. In this way, the sample holder 18 is created.

The sample holder 18 created in this way is turned upside down from the state of FIG. 3B. The first surface of the silicon nitride film 36 that is the sample-holding film 32 is made to face upward, i.e., becomes the upper surface. The first surface of the silicon nitride film 36 facing upward becomes the first surface 32*a* of the sample-holding surface 32 of the sample holder 18. The second surface 32*b* may also be made to face upward.

The thickness of the silicon nitride film 36 is set within a range of from 10 to 1,000 nm. The sample-holding film 32 of the sample holder 18 is made of silicon nitride. In addition, the film 32 may be made of silicon oxide, boron nitride, polymer, polyethylene, polyimide, polypropylene, or carbon. Where films of these materials are used, their film thicknesses are set within a range of from 10 to 1,000 nm. The sample-holding film 32 made of the aforementioned material transmits the electron beam 7 but does not transmit gas or liquid. Moreover, if the film can withstand a pressure difference of at least 1 atmosphere across the opposite surfaces of the film, then the ease of use is improved.

As the thickness of the sample-holding film 32 is reduced, scattering of the electron beam 7 is reduced and, therefore, the resolution is improved but the film is more easily damaged. As the thickness is increased, scattering of the electron beam 7 increases, resulting in decreased resolution. However, the film is less likely to be damaged. The preferable thickness of the film made of each of the above-described materials is 20 to 200 nm.

Referring back to FIG. 1, the structure of the inspection apparatus is described in further detail. A detection signal produced from the backscattered electron detector 4 is fed to an image-forming device 22 disposed outside the vacuum chamber 11. The image-forming device 22 creates image data based on the detection signal. The image data becomes image data corresponding to the SEM image.

The image data are fed to a display 23, which, in turn, displays an image based on the incoming image data. The displayed image becomes an SEM image.

The image data created by the image-forming device 22 is sent to a computer 25 if necessary. The computer 25 performs image processing on the image data and makes a decision based on the result of the image processing.

An electron beam instrument 29 equipped with the electron optical column 1 and the vacuum chamber 11 is located below the sample holder 18 and includes the backscattered electron detector 4 as well as the vacuum chamber 11 and column 1. The instrument 29 is controlled by an electron beam controller 24.

A manipulator 26 for giving a stimulus (i.e., a physical, electrical, or chemical action using voltage, chemical substance, or medicine) to the sample 20 and for moving the sample 20 if necessary and an optical microscope 27 are placed on the sample holder placement portion 12. The microscope 27 forms an optical image acquisition device and permits one to observe the sample 20 and to check the position of the tip of the manipulator 26. These components are controlled by an overall controller 28 forming overall controller. The manipulator 26 has a tip that can be brought close to or into contact with (i.e., accessible to) the sample 20 held on the first surface 32*a* of the sample-holding film 32 such that the sample is open. The above-described action is applied as a stimulus to the sample 20 via the tip. The electron optical column 1 and the optical microscope 27 are disposed opposite to each other with the sample-holding film 32 interposed therebetween.

The sample inspection apparatus according to the present invention has the electron beam instrument 29, manipulator 26, optical microscope 27, electron beam controller 24, overall controller 28, image-forming device 22, and display 23. These portions are connected with the computer 25. Information is exchanged between these portions. Thus, the sample inspection system, according to the present invention, is constituted. The overall controller 28 can control the operations of the electron optical column 1, backscattered electron detector 4, manipulator 26, and optical microscope 27.

The present apparatus can detect reactions of the sample 20 occurring before and after a stimulus is given to the sample 20 by the tip of the manipulator 26, and an SEM image can be acquired by the electron beam instrument 29 from the detected reactions. The position at which the sample 20 reacts is close to the tip of the manipulator 26. It is necessary to observe the vicinities of the position with the electron beam instrumental portion 29.

The tip of the manipulator 26 is spaced from the sample-holding film 32 under the normal usage of the apparatus. The electron beam 7 transmitted through the sample-holding film 32 gradually attenuates and thus the beam does not easily reach the tip. Even if the beam arrives, backscattered electrons produced from the tip do not easily pass through the sample-holding film 32. Therefore, it is impossible to check the position with the SEM image.

Information about the position at which the stimulus was given to the sample 20 by the tip of the manipulator 26 corresponds to information about the position of the tip of the manipulator 26. The former positional information can be derived based on information about control of motion of the manipulator 26 and on an optical image obtained by the optical microscope 27. The positional information can be entered into the electron beam controller 24 via the overall controller 28. Only a region including the position can be taken as an irradiated region and scanned with the electron beam 7. Positional information about the field of view of the optical microscope 27 is entered into the electron beam controller 24 via the overall controller 28. A region including a part or whole of the field of view can be taken as an irradiated region and scanned with the electron beam 7. This eliminates the labor to search for a region to be observed with SEM. The dose of the electron beam 7 hitting the sample 20 can be reduced to a minimum. Beam damage to the sample 20 can be reduced.

A method of inspecting a sample, in accordance with the present invention, is next described by referring to FIGS. 1 and 2.

Cell adhesion molecules, such as fibronectin and collagen, are adsorbed on the first surface 32a of the sample-holding film 32. Cells, such as nerves, are adsorbed as the sample 20 onto the first surface 32a of the sample-holding film 32 and cultured. The cell adhesion molecules play a role as an adhesive for bringing the cells close to the first surface 32a of the sample-holding film 32. Then, the sample holder 18 is placed on the sample holder placement portion 12. At this time, the open-close valve 14 is closed and in the state shown in FIG. 2. The closed space 19a closed between the open-close valve 14 and sample-holding film 32 is in the atmospheric-pressure ambient that is at normal pressure. The space in the vacuum chamber 11 that is below the open-close valve 14 is in a given vacuum state (reduced-pressure state). The inside of the electron optical column 1 in communication with the space is evacuated down to a desired vacuum level by the vacuum pump 8.

Under this condition, the closed space 19a is reduced in pressure to a vacuum using the vacuum pump 9. During this process, to prevent the sample-holding film 32 from being damaged due to rapid pressure variation from the atmospheric-pressure state, a needle valve (not shown) is used to slow down the pumpdown process to 1 to 100 seconds. The pressure is lowered from the atmospheric pressure (101,325 Pa) to a pressure of about ½ to ⅒ atm (50 kPa to 10 kPa). During this process, it is confirmed that the sample-holding film 32 of the sample holder 18 is not destroyed.

After the confirmation, the positions of the nerve cells and manipulator 26 are checked with the optical microscope 27. Minute electrodes and a microtube are installed at the tip of the manipulator 26. The minute electrodes can apply a voltage to the cell. The microtube can permit liquid to flow in and out through the microtube. Movement of the manipulator 26 makes it possible to bring the tip of the manipulator close to or into contact with the nerve cells forming the sample 20.

The minute electrodes are brought to the nerve cells closer by the movement of the manipulator 26 while illuminating the sample 20 with light and observing the sample with the optical microscope 27. A negative pressure is then applied to the microtube at the tip of the manipulator 26 to bring the microtube into intimate contact with the cell membranes. Consequently, voltage potential responses can be measured.

When the manipulator 26 is moved as described above, if the sample-holding film 32 is erroneously damaged by the manipulator 26, contamination due to diffusion of the sample 20 is restricted to within the closed space 19a because the open-close valve 14 is closed. Furthermore, if the sample-holding film 32 should be damaged and the inside of the closed space 19a be contaminated by diffusion of the sample 20, the closed space 19a can be cleaned as mentioned previously. The liquid or vapor that is the cleaning agent used for the cleaning can be discharged via the discharge tube 15 and discarded by opening the open-close valve 16. The contamination can be suppressed by coating the wall surface of the closed space 19a with boron nitride or fluororesin.

After confirming that the sample-holding film 32 carrying the sample 20 thereon is not destroyed when the closed space 19a is at a reduced-pressure state, the open-close valve 14 is opened. Consequently, the space in the vacuum chamber 11 is ceased to be partitioned off. This places the lower space in the vacuum chamber 11 into communication with the closed space 19a. Then, the light illumination for the optical microscope is ceased to prevent the light from entering the backscattered electron detector 4 via the sample-holding film 32. Other extraneous light is blocked by a shield (not shown). The shield also acts to provide radiation protection against radiation produced when the electron beam 7 irradiates the sample holder 18 and sample 20.

Then, as shown in FIG. 1, the electron beam 7 is directed from the electron optical column 1 toward the sample 20, and imaging is performed. The beam 7 is transmitted through the sample-holding film 32 of the sample holder 18 and irradiates the sample 20. Backscattered electrons produced from the sample 20 in response to the irradiation are detected by the backscattered electron detector 4. A detection signal produced from the detector 4 is fed to the image-forming device 22, which, in turn, forms image data based on the detection signal. Based on the image data, an image (SEM image) is displayed on the display 23. The image data obtained at this time is acquired as first information before a stimulus (described later) is given to the sample 20 by the manipulator 26, and is stored in the storage region of the computer 25.

Information about the position at which the manipulator 26 gives the stimulus to the sample 20 consisting of nerve cells is found at this time based on information about motion of the manipulator 26. The information is entered into the electron beam controller 24 via the overall controller 28. Therefore, only a region including the position at which the stimulus should be given to the sample 20 can be scanned with the electron beam 7. This eliminates the labor to search for a region to be observed. Electron beam damage to the sample can be reduced.

The cells to be observed have a size of tens of micrometers. If the region measures 200 μm square, for example, the region where a reaction to the stimulus given to the cells occurs can be placed within the field of view with certainty. The region may be set according to the size of the inspected object (i.e., observed object). The region can be set to within 200 μm square.

After obtaining the first information as described previously, an electric stimulus is given to the sample 20 being the nerve cells, using the minute electrodes installed at the tip of the manipulator 26. As described previously, only a region including the position at which the stimulus is given to the sample 20 is scanned with the electron beam 7. An SEM image of the sample 20 is acquired. Responsiveness of the sample 20 to the stimulus can be confirmed. At this time, the position of the region scanned with the beam 7 is determined based on the information about the position at which the stimulus was given to the sample 20 from the manipulator 26. The range of the scanned region is set to 200 μm square or less.

Image data obtained at this time becomes second information after application of the electric stimulus. The second information is also stored in the storage region of the computer 25. The computer 25 can particularly confirm the responsiveness of the cells by comparing the first information with the second information.

After performing imaging (i.e., acquisition of the second information) subsequently to the application of the stimulus to the sample 20, the open-close valve 14 is closed. This can prevent contamination of the electron optical column 1 in a case where the sample-holding film 32 is destroyed. Alternatively, imaging is performed (acquisition of the first information) prior to application of the stimulus to the sample 20, and then the open-close valve is once closed. Under this condition, a stimulus is given to the sample 20 from the manipulator 26. Then, the open-close valve 14 is opened and subsequently the second information is acquired.

In some cases, before variations occurring after a stimulus is given to the cells are observed with SEM as described above, the variations may be observed with the optical microscope 27. In these cases, if the open-close valve 14 is closed, risk of contamination can be reduced should the film be broken. In any case, the probability of contamination of the inside of the apparatus can be reduced by shortening the interval for which the open-close valve 14 is opened during inspection of the sample 20. This is achieved by closing the open-close valve 14 when the sample 20 is not irradiated with the electron beam 7.

Where the speed of reaction of the cells to the stimulus is low, the open-close valve 14 may be once closed. The valve 14 may be again opened at a time when a reaction is deemed to have taken place. Then, imaging may be performed using the electron beam 7. The reaction can be checked with the optical microscope 27.

A mechanism capable of spraying a chemical substance or medicine can be installed at the tip of the manipulator 26. Behavior of the cells in response to the chemical substance or medicine can be observed while observing the cells with SEM. Furthermore, a function of permitting fluid to flow out can be imparted to the manipulator 26. This permits the sprayed substance to be recovered.

When the manipulator 26 is being manipulated, if the sample-holding film 32 is erroneously destroyed, it is necessary to prevent contamination of the electron optical column 1. For this purpose, the following method can be used. Information about the position of the sample-holding film 32 is obtained by performing a measurement, for example, using an optical microscope or laser measuring equipment (not shown). Information about the position of the manipulator 26 is acquired based on information about control of motion of the manipulator 26, and the sample-holding film 32 and manipulator 26 are prevented from being overlapped in position. If the positions nearly overlap, then a warning is displayed or issued, the operation of the manipulator 26 is stopped, and/or the open-close valve 14 is closed.

In another method, a voltage is applied between the sample-holding film 32 and the manipulator 26, and a variation in the voltage, current, or resistance between the film 32 and manipulator 26 is measured. A variation in voltage, current, or resistance caused when the manipulator 26 touches the sample-holding film 32 is detected. A warning is displayed or issued, the operation of the manipulator 26 is stopped, and/or the open-close valve 14 is closed. This method can reduce the probability of destruction of the sample-holding film 32. If it should be destroyed, contamination of the electron optical column 1 can be prevented.

Furthermore, when the manipulator 26 is being manipulated, if the tip of the manipulator 26 touches the sample-holding film 32, and if an unwanted external force is applied to the film 32 from the tip, the film 32 may be damaged. In this case, destruction of the sample-holding film 32 is induced. If so, the sample 20 held on the film 32 will leak into the vacuum chamber 11 and into the electron optical column 1 and diffuse. As a result, the apparatus will be contaminated.

Therefore, in the present invention, when the manipulator 26 is being manipulated, the operation of the manipulator 26 is controlled by the overall controller 28 to prevent the tip of the manipulator 26 from touching the sample-holding film 32 (i.e., to circumvent contact between the tip and the film 32). Consequently, the tip of the manipulator 26 does not damage the sample-holding film 32. Hence, destruction of the film 32 due to manipulation of the manipulator 26 can be prevented.

To achieve the above-described object, the present invention provides a first technique. This consists of measuring the position of the sample-holding film 32 in the z-direction (vertical direction) using a measuring device made of the optical microscope 27 or laser measuring equipment (not shown). The results of the measurement, i.e., positional information, are sent to the overall controller 28.

At the same time, the overall controller 28 obtains positional information (information about the position in the z-direction) about the tip of the manipulator 26, based on information about control of motion of the manipulator 26. The overall controller 28 controls the operation of the manipulator 26 to prevent the z-position of the sample-holding film 32 from overlapping the z-position of the tip of the manipulator 26.

In particular, when the tip of the manipulator 26 approaches the sample-holding film 32, if the spacing between the tip and the film 32 taken in the z-direction decreases and reaches a given distance set as a margin, the overall controller 28 limits the operation of the manipulator 26 such that at least operation in the z-direction is stopped. At this time, the overall controller 28 may issue a warning instead of or in addition to the limitation on the operation of the manipulator 26.

When the spacing reaches a preset distance shorter than the given distance, the overall controller 28 may issue a warning instead of or in addition to the limitation on the operation of the manipulator 26. That is, when the spacing reaches the preset distance and the tip of the manipulator 26 touches the sample-holding film 32, the overall controller 28 may issue a warning instead of or in addition to the limitation on the operation of the manipulator 26. In this case, the tip of the manipulator 26 touches the film 32. At this instant of time, the operation of the manipulator 26 is restricted and, therefore, application of an unwanted external force to the sample-holding film 32 from the tip can be prevented.

The present invention also provides a second technique. In this second technique, a voltage is applied between the tip of the manipulator 26 and the sample-holding film 32 by voltage application means (not shown). An electrical or physical amount, such as a voltage value, current value, or resistance value between the tip and the sample-holding film 32, is detected by detection means (not shown). The result of the detection performed by the detection means is sent to the overall controller 28. The overall controller 28 controls the operation of the manipulator 26 based on the result of the detection using the detection means to prevent the tip of the manipulator 26 from touching the sample-holding film 32.

The overall controller 28 controls the manipulator 26 to stop the operation at least in the z-direction when the overall controller has determined based on the result of the detection that the spacing between the tip of the manipulator 26 and the sample-holding film 32 has reached the given distance. At this time, the overall controller 28 may issue a warning instead of or in addition to the limitation on the operation of the manipulator 26.

In the same way as the foregoing, when the spacing has reached the preset distance shorter than the given distance, the overall controller 28 may issue a warning instead of or in addition to the limitation on the operation of the manipulator 26. Especially, at the instant when the tip of the manipulator 26 touches the film 32, the operation of the manipulator 26 is limited. Therefore, application of an unwanted external force to the sample-holding film 32 from the tip can be prevented. Contact between the tip and the film 32 can be detected by detecting a variation in voltage, current, or resistance between them.

In the first and second techniques, the open-close valve 14 may be closed in addition to limitation on the operation of the manipulator 26 or issuance of a warning.

These methods make it possible to prevent destruction of the sample-holding film 32. If the sample-holding film 32 is destroyed, contamination of the apparatus including the electron optical column 1 can be prevented.

In the present embodiment, fibronectin is used to adsorb the sample 20 onto the sample-holding film 32. Instead, poly-L-lysine and collagen may be used.

In the foregoing, backscattered electrons are used as electrons detected for forming an image (SEM image). Backscattered electrons produce a signal intensity proportional to the atomic number. Therefore, where the sample is almost totally made of substances of low atomic numbers, such as a biological sample, the image contrast is very low, and it is difficult to improve the resolution. Accordingly, a heavy metal, such as gold, may be adsorbed onto portions of the cells to be noticed in their behavior. In particular, gold is adsorbed onto the portions (antigen) via an antibody by causing the antigen tagged with gold particles having the nature of being adsorbed on the portions (antigen) to be sprayed into the cells, so that gold is adsorbed onto the portions (antigen) via the antibody by making use of an antigen-antibody reaction. Furthermore, a fluorescent substance (fluorescent dye or quantum dots (e.g., nanoparticles of Si)) that emits light when irradiated with an electron beam may be previously adsorbed onto cell portions of interest, and the fluorescent light may be observed with an optical microscope.

As described so far, use of the present invention makes it possible to observe or inspect a reaction of living cells to a stimulus at high resolution with SEM, which has been impossible to achieve with the prior art technique.

In the above embodiment, nerve cells are used. Besides, various tissue cells including adrenal cortex cells, cardiac muscle cells, stomach cells, intestinal cells, and cells of blood vessels can be observed. Furthermore, the present invention can also be applied to a reaction inspection system that investigates reactions of cells to pharmaceuticals. Examples of this are given below.

1. Hypertension

In order to lower the blood pressure of a person with hypertension, it is necessary to block the action of ion channels (especially, potassium channels) present in the blood vessels, for stretching the blood vessels. In development of medicines producing such effects, it is important to directly observe reactions of the potassium ions to dispersion of medicine. Examples of observation using the present invention are shown below.

First, cells of blood vessels are cultivated as the sample 20 on the sample-holding film 32. The size of the potassium channels to be observed is as small as 7 to 9 nm. The atoms constituting the channels have small atomic numbers. Therefore, a backscattered electron image has low contrast, and it is difficult to observe the sample as described previously. Accordingly, in order to improve the contrast, an antibody previously tagged with a gold marker is adsorbed onto the potassium channels (i.e., antigen) by utilizing an antigen-antibody reaction. The antibody acts against extracellular loops of potassium channels. Because the efficiency of emission of backscattered electrons from gold is high, it is easy to observe the positions of the potassium channels with SEM. Then, the tip of the manipulator 26 is brought close to the cells, and a medicinal solution is sprayed. Before and after the spraying of the medicinal solution, the cells are scanned with the electron beam 7 via the sample-holding film 32. Produced backscattered electrons are detected by the detector 4. The resulting detection signal is fed to the image-forming device 22. An SEM image can be displayed on the image display 23. Consequently, agglutination of the potassium channels on the medicinal solution can be observed. It is known that there is a close relationship between the action of potassium channels and the agglutination. The method developed as disclosed herein can contribute to pharmaceutical applications.

Besides, ion channels are associated with many diseases including arrhythmia and muscular diseases and disorders. Cells with these diseases can be used for development of pharmaceuticals. Diabetes insipidus due to abnormalities with the kidney is induced by inability of water channels present in renal tubules to react. With respect to this disease, too, application to observation and development of pharmaceuticals is made possible by a similar method.

2. Diabetes

Diabetes is caused by an abnormality in membrane transport of glucose transporter-4 (GLUT4) that accepts increased concentrations of blood glucoses into cells to reduce blood sugar. The glucose transporter is specifically developed in muscles and fat tissues. Using the present invention, medicines are given to the glucose transporter, and morphological variations occurring in the cells are observed. The results can be utilized for discovery of new drugs for diabetes and methods of treatment. First, fat tissues are cultivated as the sample 20 on the sample-holding film 32. The tip of the manipulator 26 is brought close to the cultivated cells while observing them with the optical microscope 27. A medicinal solution is sprayed from the tip of the manipulator 26. Before and after the spraying of the medicinal solution, the cells are scanned with the electron beam 7 via the film 32. Produced backscattered electrons are detected by the detector 4. The resulting detection signal is fed to the image-forming device 22, and an SEM image can be displayed on the image display 23. Consequently, reactions of the cells to the medicine can be observed. In this way, the present invention can contribute to developments of medicines that are effective for diabetes.

3. Influenza

When influenza viruses are adsorbed onto receptors on the surfaces of cells, the cells become infected with the viruses. A miracle drug against influenza prevents the adsorption. In the past, it has been difficult to directly observe the adsorption. It has taken an exorbitantly long time to develop a miracle dug. For example, there is a method of making an observation with an optical microscope by tagging influenza viruses with fluorescent markers. In this method, it is impossible to discriminate whether the cells are phagocytic cells eating influenza viruses (not infected) or the influenza viruses have been adsorbed on the cells (i.e., infected). However, use of the present invention makes possible the discrimination. First, cells are cultivated as the sample 20 on the sample-holding film 32. Influenza viruses tagged with gold particles are sprayed from the tip of the manipulator 26 into the cells. Then, a medicinal solution is sprayed into the cells with another manipulator. Under this condition, the cells are scanned with the electron beam 7 via the sample-holding film 32. Produced backscattered electrons are detected by the detector 4. The resulting detection signal is fed to the image-forming device 22, and an SEM image can be displayed on the image display 23. The image makes it possible to confirm the degree of adsorption of the influenza viruses on the cells. Where the medicine is efficacious, it can be confirmed that there is no adsorption of the influenza viruses onto the cells. Even if the cells have eaten the influenza viruses, i.e., the cells are phagocytic cells, a high-resolution SEM image is obtained. It is possible to check the positions of the influenza viruses and cells. Infection and phagocytic action can be discriminated. In this way, the present invention can contribute to development of miracle drugs against influenza.

4. Depression

Depression is caused by a disorder of secretion of a neuro-neuro transmitter from nerve cells. The potential inside the cell membranes varies toward the positive side (+) when Ca (2+) ions (positive bivalent potassium ions) flow in, causing the cellules in the cells to merge with the cell membranes. As a result, a neuro-neuro transmitter is secreted. Therefore, the cells are cultivated as the sample 20 on the sample-holding film 32. The tip of the manipulator 26 is brought close to the cells. The cells are observed with SEM while giving an electric stimulus to the cells using the manipulator. Consequently, behaviors of the cellules in the cells can be elucidated. Furthermore, a medicament acting on membrane proteins is sprayed, and the resulting variations are observed. This can contribute to development of pharmaceuticals. Such secretion of a neuro-neuro transmitter and abnormal release of transmitters are associated with various diseases and provide valuable information for medical science and development of pharmaceuticals.

In the above embodiment, the normally used gold marker has particle diameters of 10 to 30 mm. However, the adsorptive force between the antibody and gold marker is weak. In some cases, gold markers of 10 to 30 nm cannot be attached. In these cases, very small gold particles (nanogold particles) having particle diameters of the order of nanometers are first attached to the antibody. Under this condition, the gold particles are too small and it is difficult to observe them with SEM. Silver is adsorbed around the gold particles by making use of a silver sensitizer. This makes it easier to detect them with SEM.

An inspection system for selecting pharmaceuticals effective against diseases can be created by performing image processing with the computer 25 based on image data created by the image-forming device 22, extracting features, such as a shape, and comparing the extracted features against a database of cell shapes for which previously prepared drugs have been effective.

Embodiment 2

Where the resistance of the sample-holding film 32 is sufficient, an inspection apparatus (FIG. 4) from which the open-close valve 14 has been omitted can also be used. The structure of the apparatus is simplified. The cost of the apparatus can be reduced. Furthermore, the working distance between the sample and the electron optical column 1 can be reduced. This leads to an improvement of the resolution and to an improvement of the efficiency at which backscattered electrons are detected. Images of higher quality can be captured.

Embodiment 3

Figure 5:
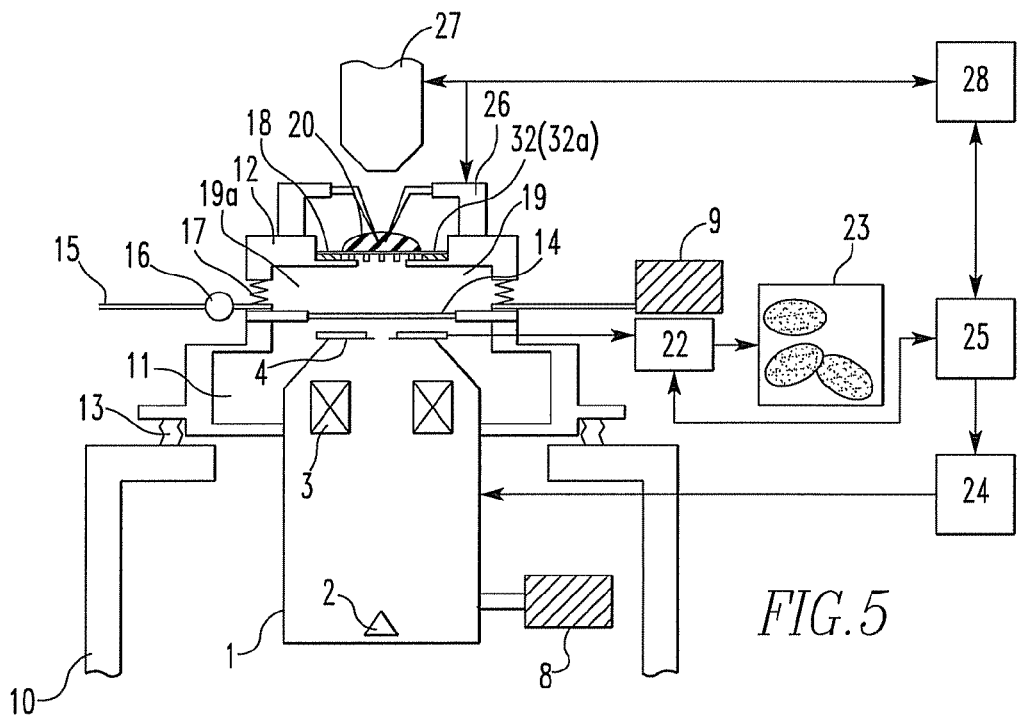
FIG. 5 is a schematic diagram showing a third embodiment of the sample inspection apparatus according to the present invention.

As shown in FIG. 5, driver 17 having a bellows structure is mounted between an open-close valve 14 and a sample holder placement portion 12 in a vacuum chamber 11. Consequently, a sample holder 18 and a sample-holding film 32 formed on the holder can move vertically and horizontally independent of an optical microscope 27 and an electron optical column 1. Accordingly, if a region that can be irradiated with an electron beam 7 greatly deviates in position from an observed region of the sample 20, the irradiated region can be made to overlap the observed region by moving the sample holder 18.

If the optical axis of the optical microscope 27 is aligned with the optical axis of the electron optical column 1 within a tolerance range of less than 50 μm, or if the center of the field of view of the optical microscope 27 (the center of the optical image) is aligned with the center of the field of view of the SEM image (the center of the region irradiated with the electron beam 7) within a tolerance range of less than 50 μm, the object to be observed is checked with the optical microscope 27 by moving the sample holder 18. At the same time, the observed object is captured within the SEM image, thus offering convenience.

Since the size of the cells to be observed is about tens of micrometers, it is advantageous if the deviation of the optical axis or the center of the field of view is less than 50 μm. Where this structure is not used, the coordinates of the field of view of the optical microscope 27 or information about the position of the manipulator 26 is entered into the electron beam controller 24 via the overall controller 28 as already described in Embodiment 1. Only a region including the position may be scanned with the beam 7.

The three-dimensional structure of the inspected object can also be checked by rotating or tilting the sample holder 18 using the driver 17 and performing an inspection. In these cases, if secondary electrons or backscattered electrons produced from the sample 20 are detected by two or more detectors, the three-dimensional structure can be checked more clearly.

Embodiment 4

Figure 6:
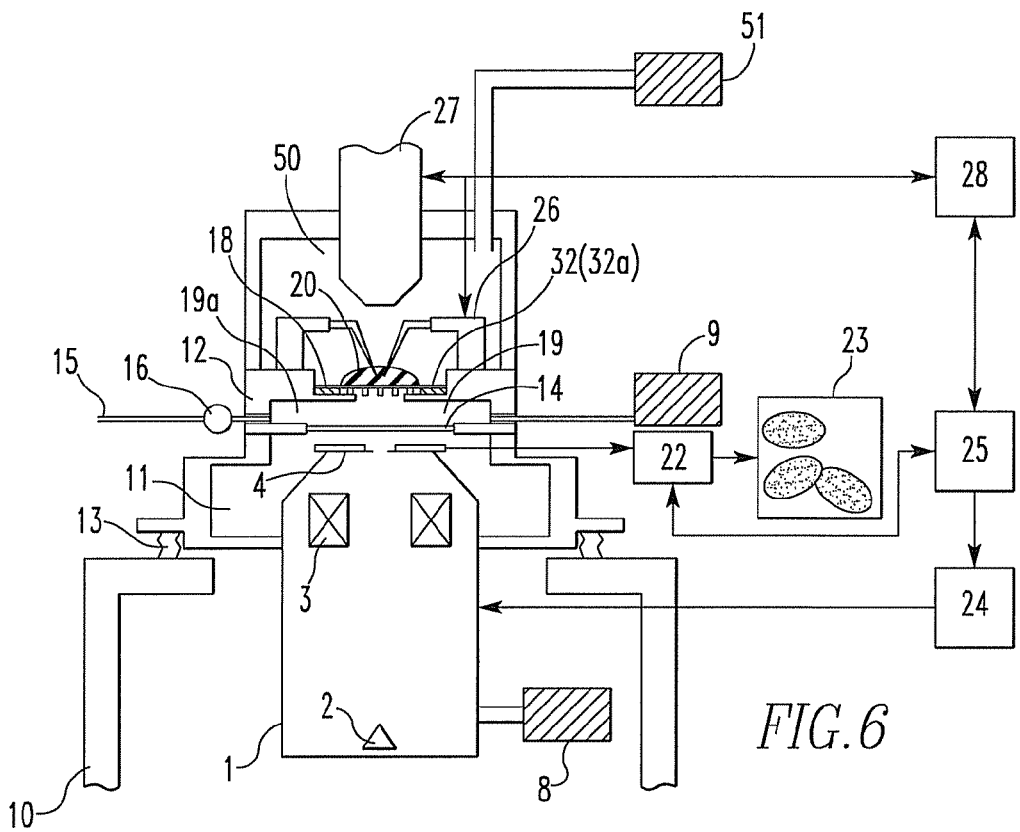
FIG. 6 is a schematic diagram showing a fourth embodiment of the sample inspection apparatus according to the present invention.

Embodiment 4 of the present invention is next described by referring to FIG. 6. To reduce the probability of destruction of a sample-holding film 32, a detachable pressure-adjusting chamber 50 and evacuatable pressure-adjusting means 51 connected with the chamber 50 are mounted over a sample holder placement portion 12 as shown in FIG. 6. Thus, the sample holder 18 is located within the pressure-adjusting chamber 50. The pressure of the ambient in contact with the first surface 32*a* of the sample-holding film 32 can be adjusted and reduced. The pressure-adjusting chamber is also used to provide radiation protection against radiation produced when electron beam irradiation is performed and to block extraneous light.

When an inspection is performed using the apparatus of this structure, an open-close valve 14 is closed. A closed space 19*a* closed between the open-close valve 14 and the sample-holding film 32 is in an atmospheric-pressure ambient that is at normal pressure. At this time, the pressure-adjusting chamber 50 is not located above the sample holder placement portion 12.

The space in the vacuum chamber 11 that is located below the open-close valve 14 is at a desired vacuum level (reduced-pressure state). The inside of the electron optical column 1 in communication with the space is evacuated by vacuum pump 8 and reduced in pressure to a desired vacuum level.

Under this condition, the sample 20 is adsorbed on the upper surface 32*a* of the sample-holding film 32 of the sample holder 18 and cultivated. Then, the pressure-adjusting chamber 50 is brought to a position located above the sample holder placement portion 12. As a result, the sample 20 placed on the sample-holding film 32 of the sample holder 18 is placed inside the pressure-adjusting chamber 50.

Then, the closed space 19*a* is evacuated by the pump 9 and, at the same time, the inside of the pressure-adjusting chamber 50 is reduced in pressure by the pressure-adjusting means 51. The pressure of the ambient inside the pressure-adjusting chamber 50 is set to about ½ atm (about 50 kPa), for example. Consequently, the pressure difference between the chamber 50 and the ambient is reduced. This reduces the external force applied to the sample-holding film 32 due to the pressure difference. Hence, the frequency of damage to the sample-holding film 32 can be reduced. Evaporation of the moisture contained in the sample 20 can be prevented by setting the pressure in the pressure-adjusting chamber to greater than the water vapor pressure. As the need arises, the sample 20 may be cooled to lower the water vapor pressure.

In the above-described Embodiments 1-4, living cells can be observed with SEM. Furthermore, a reaction to a stimulus applied to the cells can be inspected. In the above embodiments, backscattered electrons are used as a secondary signal. Besides, information about the sample 20 can be obtained by detecting secondary electrons, X-rays, or cathode luminescence light produced in response to irradiation of the sample 20 by the electron beam 7. Additionally, an electrical current absorbed by the sample 20 in response to the irradiation can also be detected. Measurement of the absorption current can be performed conveniently if the manipulator 26 is used.

In the present embodiment, the sample-holding film 32 is made of silicon nitride. It is advantageous if the film withstands a pressure difference of at least 1 atm. The embodiment is characterized in that gas or liquid does not flow in or out. Specifically, the material of the film 32 includes at least one of polymer, polyethylene, polyimide, polypropylene, carbon, silicon oxide, silicon nitride, and boron nitride. The thickness of the film is 10 to 1,000 nm. Optical opaqueness can be imparted to the sample-holding film 32 by vapor-depositing a light-element metal, such as aluminum, onto the film to a thickness of 40 nm, for example. Incidence of extraneous light on the backscattered electron detector 4 is prevented. The optical microscope and SEM can be observed at the same time.

In the above embodiments, an electron beam is used as the primary beam. If the sample-holding film 32 shows sufficient shock resistance and strength against impingement of other charged-particle beams, such as a helium ion beam, the invention can also be applied if the other charged-particle beam is used. In the present invention, an inverted SEM is used. If normal non-inverted SEM is used, no problem takes place.

In this way, a sample inspection apparatus according to the present invention has: electron optical column 1 for irradiating the sample 20 with the primary beam 7 via the film 32; and backscattered electron detector 4 for detecting a secondary signal produced from the sample 20 in response to the beam irradiation. The sample inspection apparatus is characterized in that it further includes: the manipulator 26 having a tip capable of being brought close to or into contact with the sample 20; the optical microscope 27 for acquiring an optical image of the sample 20; and the overall controller 28 for controlling the operations of the primary beam irradiation column 1; backscattered electron detector 4; manipulator 26, and optical microscope 27.

Another sample inspection apparatus, according to the present invention, has: the film 32 having a first surface on which a sample is held; the vacuum chamber 11 for reducing the pressure of the ambient in contact with a second surface of the film 32; the electron optical column 1 connected with the vacuum chamber 11 and irradiating the sample 20 with the primary beam 7 via the film 32; and the backscattered electron detector 4 for detecting a secondary signal produced from the sample 20 in response to the beam irradiation. The sample inspection apparatus further includes: the manipulator 26 having a tip capable of being brought close to or into contact with the sample 20; the optical microscope 27 for acquiring an optical image of the sample 20; and the overall controller 28 for controlling the operations of the electron optical column 1, backscattered electron detector 4; manipulator 26, and optical microscope 27.

At this time, the first surface of the film 32 is the first surface (upper surface) of the film 32. The second surface of the film 32 is the lower surface of the film 32. However, where the electron optical column 1 is not of the inverted type, the first surface may be the lower surface of the film 32, and the second surface may be the upper surface of the film 32.

There is further provided the open-close valve 14 for partitioning off the space between the film 32 and the electron optical column 1 within the vacuum chamber 11. The electron optical column 1 and the optical microscope 27 are disposed opposite to each other with the film 32 interposed therebetween.

The overall controller 28 can determine the region irradiated with the primary beam 7 emitted from the electron optical column 1 based on information about the position of the tip of the manipulator 26. This permits the portion of the sample 20 located close to the tip of the manipulator 26 to be irradiated with the primary beam 7.

The overall controller 28 obtains information about the position of the tip of the manipulator 26 based on an optical image acquired by the optical microscope 27 and determines the region irradiated with the primary beam 7 emanating from the electron optical column 1 based on the positional information. Consequently, a portion of the sample 20 located close to the tip of the manipulator 26 can be irradiated with the primary beam 7.

Furthermore, the overall controller 28 determines the region irradiated with the primary beam 7 produced from the electron optical column 1 based on the field of view of the optical microscope 27. This enables the region corresponding to the field of view to be irradiated with the primary beam 7.

At this time, the optical axis of the electron optical column 1 is preferably aligned with the optical axis of the optical microscope 27 within a tolerance range of less than 50 μm. Alternatively, the center of the region irradiated with the primary beam 7 produced from the electron optical column 1 is preferably aligned with the center of the optical image acquired by the optical microscope 27 within a tolerance range of less than 50 μm.

The driver (film-moving device) 17 for moving the film 32 can be added. The manipulator 26 can perform at least one of an operation for making contact with the sample 20, an operation for suction, an operation for supplying liquid into the sample 20 or discharging the liquid from it, and an operation for supplying electricity to the sample 20.

The film 32 includes at least one of polymer, polyethylene, polyimide, polypropylene, carbon, silicon oxide, silicon nitride, and boron nitride. The thickness of the film is set within a range of from 10 to 1,000 nm.

The primary beam 7 is not limited to an electron beam. The primary beam can be another charged-particle beam, such as an ion beam. The secondary signal can be at least one kind of backscattered electrons, secondary electrons, absorption current, cathode luminescence light, and X-rays.

The region irradiated with the primary beam 7 can measure 200 μm square or less. Furthermore, the absorption current in the sample 20 can be detected via the manipulator 26.

The sample 20 includes an antigen that is an element of the living body. An antibody tagged with a metal or fluorescent substance may be coupled to the antigen.

A sample inspection method according to the present invention is implemented to inspect a sample using the above-described sample inspection apparatus.

Furthermore, in the sample inspection method according to the present invention, the sample 20 is irradiated with the primary beam 7 from the electron optical column 1 via the film 32. Information (first information) about the sample 20 is obtained in response to the irradiation. A physical, electrical, or chemical action is applied to the sample 20. After the application, the sample 20 is irradiated with the primary beam 7 via the film 32. Information (second information) about the sample 20 is obtained in response to the irradiation. The first information is compared with the second information.

At this time, a physical, electrical, or chemical action can be applied to the sample 20 using the manipulator 26. When the physical, electrical, or chemical action is applied to the sample 20, the space between the film 32 and the electron optical column 1 can be partitioned off by the open-close valve 14.

The sample inspection system according to the present invention has the above-described sample inspection apparatus. In addition, the system has the computer 25 (information-processing means) for making a decision about the sample 20 from information based on a secondary signal from the sample 20, the secondary signal being detected by the sample inspection apparatus.

Furthermore, in the sample inspection method according to the present invention, a secondary signal from the sample 20 can be detected using the sample inspection apparatus, and a decision about the sample 20 can be made from the information about the sample 20 based on the secondary signal.

In the sample inspection system and sample inspection method, a physical, electrical, or chemical action can be applied to the sample 20 using the manipulator 26. After the application, a decision can be made about the sample 20 based on information about the sample 20.

Different pieces of information about the sample 20 are obtained before and after a physical, electrical, or chemical action is applied to the sample 20 using the manipulator 26. The pieces of information are compared. Based on the results of the comparison, a decision can be made about the sample 20.

At this time, where the sample 20 contains a part of a living organism, a chemical substance is supplied into the sample 20 by the manipulator 26. The effectiveness of the chemical substance for the living organism can be judged based on information about the sample 20 after the supply of the chemical substance.

Where the sample 20 contains a part of a living organism, a decision can be made as to whether the living organism has any disease.

In the above embodiments, information about the sample 20 is image data about the sample 20.

In the present invention, the sample 20 is irradiated with the primary beam 7 via the film 32. A secondary signal produced from the sample 20 in response to the beam irradiation can be detected. The sample 20 can be manipulated with the manipulator 26. An optical image of the sample can be obtained.

At this time, the sample 20 can be observed with SEM without evaporating the liquid surrounding the sample 20 by placing the sample 20 in a normal-pressure ambient. Furthermore, a stimulus can be given to the sample 20 using the manipulator 26. The resulting reactions (including reactions occurring before and after the application of the stimulus) can be observed.

The dose of the primary beam 7 impinging on the film 32 and on the sample 20 can be reduced to a minimum by restricting the range irradiated with the primary beam 7 to surroundings of the portion of the sample 20 to which the stimulus was given by the manipulator 26, using positional information about the manipulator 26. Damage to the film 32 and sample 20 by the primary beam 7 can be reduced.

Even where the film 32 is destroyed by the manipulator 26, contamination of the inside of the apparatus can be prevented by providing the open-close valve 14 for partitioning off the space between the film 32 and the electron optical column 1.

Additionally, a sample inspection apparatus according to the present invention has: electron beam optical column for irradiating a sample 20 with a primary beam 7 via a film 32; backscattered electron detector 4 for detecting a secondary signal produced from the sample 20 in response to the beam irradiation; a manipulator 26 having a tip that can be brought close to or into contact with the sample 20; measurement means for measuring the position of the film 32; and overall controller 28 for controlling the operations of the electron optical column 1, backscattered electron detector 4, manipulator 26, and measurement means. The overall controller 28 controls the operation of the manipulator 26 based on the result of the measurement performed by the measurement means such that contact of the tip of the manipulator 26 with the film 32 is avoided or the operation of the manipulator 26 is restricted when the tip is in contact with the film.

Another sample inspection apparatus according to the present invention has: a film 32 having a first surface 32a on which a sample 20 is held; a vacuum chamber 11 for reducing the pressure of an ambient in contact with a second surface of the film 32; electron optical column 1 connected with the vacuum chamber 11 and irradiating the sample 20 with a primary beam 7 via the film 32; backscattered electron detector 4 for detecting a secondary signal produced from the sample 20 in response to the beam irradiation; a manipulator 26 having a tip that can be brought close to or into contact with the sample 20; measurement means for measuring the position of the manipulator relative to the film 32; and overall controller 28 for controlling the operations of the electron optical column 1, backscattered electron detector 4, manipulator 26, and measurement means. The overall controller 28 controls the operation of the manipulator 26 based on the result of the measurement performed by the measurement means such that contact of the tip of the manipulator 26 with the film 32 is avoided or the operation of the manipulator 26 is restricted when the tip is in contact with the film.

A further sample inspection apparatus according to the present invention has: electron optical column 1 for irradiating a sample 20 with the primary beam 7 via a film 32; backscattered electron detector 4 for detecting a secondary signal produced from the sample 20 in response to the beam irradiation; a manipulator 26 having a tip that can be brought close to or into contact with the sample 20; manipulator position detection means for detecting an electrical or physical amount (such as a voltage value, current value, or resistance value) between the tip of the manipulator 26 and the film 32; and overall controller 28 for controlling the operations of the electron optical column 1, backscattered electron detector 4, manipulator 26, and manipulator position detection means. The overall controller 28 controls the operation of the manipulator 26 based on the result of the detection performed by the manipulator position detection means such that contact of the tip of the manipulator 26 with the film 32 is avoided or the operation of the manipulator 26 is restricted when the tip is in contact with the film.

Still another sample inspection apparatus according to the present invention has: a film 32 having a first surface 32a on which a sample 20 is held; a vacuum chamber 11 for reducing the pressure of an ambient in contact with a second surface of the film 32; electron optical column 1 connected with the vacuum chamber 11 and irradiating the sample 20 with a primary beam 7 via the film 32; backscattered electron detector 4 for detecting a secondary signal produced from the sample 20 in response to the beam irradiation; a manipulator 26 having a tip that can be brought close to or into contact with the sample 20; manipulator position detection means for detecting an electrical or physical amount (such as a voltage value, current value, or resistance value) between the tip of the manipulator 26 and the film 32; and overall controller 28 for controlling the operations of the electron optical column 1, backscattered electron detector 4, manipulator 26, and manipulator position detection means. The overall controller 28 controls the operation of the manipulator 26 based on the result of the detection performed by the manipulator position detection means such that contact of the tip of the manipulator 26 with the film 32 is avoided or the operation of the manipulator 26 is restricted when the tip is in contact with the film.

The surface (first surface) 32a of the film 32 on the side of the sample 20 is electrically conductive. The surface (first surface) 32a of the film 32 on the side of the sample 20 is the upper surface of the film 32, while the surface (second surface) 32b facing away from the first surface is the lower surface of the film 32.

When it is detected based on the result of the measurement or detection performed by the measurement means or manipulator position detection means that the spacing between the tip of the manipulator 26 and the film 32 is less than a given distance, the overall controller 28 limits the operation of the manipulator 26 or issues a warning.

When it is detected based on the result of the measurement or detection performed by the measurement means or manipulator position detection means that the spacing between the tip of the manipulator 26 and the film 32 is less than a given distance, the overall controller 28 can drive open-close valve 14 to partition off the space between the film 32 and the electron optical column 1 by further providing the open-close valve 14 for partitioning off the space.

There is further provided the optical microscope 27. The optical microscope 27 and the electron optical column 1 are disposed opposite to each other with the film 32 interposed therebetween. The optical microscope 27 permits the position of the film 32 to be measured.

The manipulator 26 can perform at least one of an operation for making contact with the sample 20, an operation for suction, an operation for supplying liquid into the sample 20 or discharging the liquid from it, and an operation for supplying electricity to the sample 20.

The film 32 includes at least one of polymer, polyethylene, polyimide, polypropylene, carbon, silicon oxide, silicon nitride, and boron nitride. The thickness of the film is set to a range of from 10 to 1,000 nm.

The primary beam 7 is an electron beam or ion beam. The secondary signal can be at least one kind of backscattered electrons, secondary electrons, absorption current, cathode luminescence light, and X-rays.

A sample inspection method according to the present invention is implemented to inspect a sample using the above-described sample inspection apparatus.

A sample inspection method according to the present invention starts with irradiating a sample 20 with a primary beam 7 via a film 32. A secondary signal produced from the sample 20 in response to the beam irradiation is detected. The tip of a manipulator 26 is brought close to or into contact with the sample 20. The position of the film 32 is measured. The operation of the manipulator 26 is controlled based on the result of measurement such that contact of the tip of the manipulator 26 with the film 32 is avoided or the operation of the manipulator 26 is restricted when the tip is in contact with the film.

Another sample inspection method according to the present invention starts with holding a sample 20 on a first surface 32a of a film 32. The pressure of an ambient in contact with a second surface of the film 32 is reduced. The sample 20 is irradiated with a primary beam 7 via the film 32. A secondary signal produced from the sample 20 in response to the beam irradiation is detected. The tip of the manipulator 26 is brought close to or into contact with the sample 20. The position of the film 32 is measured. The operation of the manipulator 26 is controlled based on the result of measurement such that contact of the tip of the manipulator 26 with the film 32 is avoided or the operation of the manipulator 26 is restricted when the tip is in contact with the film. The position of the film 32 can be measured by an optical microscope 27.

A further sample inspection method according to the present invention starts with irradiating a sample 20 with a primary beam 7 via a film 32. A secondary signal produced from the sample 20 in response to the beam irradiation is detected. The tip of the manipulator 26 is brought close to or into contact with the sample 20. An electrical or physical amount (such as a voltage value, current value, or resistance value) between the tip of the manipulator 26 and the film 32 is detected. The operation of the manipulator 26 is controlled based on the result of the detection such that contact of the tip of the manipulator 26 with the film 32 is avoided or the operation of the manipulator 26 is restricted when the tip is in contact with the film.

Still another sample inspection method, according to the present invention, starts with holding a sample 20 on a first surface 32a of a film 32. The pressure of an ambient in contact with a second surface of the film 32 is reduced. The sample 20 is irradiated with a primary beam 7 via the film 32. A secondary signal produced from the sample 20 in response to the beam irradiation is detected. The tip of the manipulator 26 is brought close to or into contact with the sample 20. An electrical or physical amount (such as a voltage value, current value, or resistance value) between the tip of the manipulator 26 and the film 32 is detected. The operation of the manipulator 26 is controlled based on the result of the detection such that contact of the tip of the manipulator 26 with the film 32 is avoided or the operation of the manipulator 26 is restricted when the tip is in contact with the film. The surface (first surface) 32a of the film 32 on the side of the sample 20 is electrically conductive.

The surface (first surface) 32a of the film 32 on the side of the sample 20 is the upper surface of the film 32. The surface (second surface) of the film 32 facing away from the first surface is the lower surface of the film 32.

When it is detected based on the result of the measurement or detection that the spacing between the tip of the manipulator 26 and the film 32 is less than a given distance, the operation of the manipulator 26 is limited or a warning is issued.

When it is detected based on the result of the measurement or detection that the spacing between the tip of the manipulator 26 and the film 32 is less than a given distance, the space between the film 32 and the electron optical column 1 can be partitioned off.

The manipulator 26 can perform at least one of an operation for making contact with the sample 20, an operation for suction, an operation for supplying liquid into the sample 20 or discharging the liquid from it, and an operation for supplying electricity to the sample 20.

The film 32 includes at least one of polymer, polyethylene, polyimide, polypropylene, carbon, silicon oxide, silicon nitride, and boron nitride. The thickness of the film is set to a range of 10 to 1,000 nm.

The primary beam 7 is an electron beam or ion beam. The secondary signal can be at least one kind of backscattered electrons, secondary electrons, absorption current, cathode luminescence light, and X-rays.

In this way, in the present invention, the operation of the manipulator 26 is controlled based on the result of the measurement of the position of the film 32 or on the result of the detection of an electrical or physical amount between the tip of the manipulator 26 and the film 32 such that contact of the tip of the manipulator 26 with the film 32 is avoided or the operation of the manipulator 26 is restricted when the tip is in contact with the film.

Consequently, contact of the tip of the manipulator 26 with the film 32 can be prevented or application of an unwanted external force to the film 32 due to the tip of the manipulator 26 when the tip is in contact with the film can be prevented. Generation of damage to the film 32 due to operation of the manipulator 26 can be prevented with certainty.

As a result, during observation or inspection of the sample 20 on the film 32 by SEM, it is unlikely that the film 32 is destroyed by the manipulator 26; otherwise, the sample 20 would be diffused, contaminating the apparatus.

The provision of the open-close valve 14 makes it possible to partition off the space between the film 32 and the electron optical column 1 when the tip of the manipulator 26 is in contact with the film 32 or immediately before the tip touches the film. Consequently, if the film 32 is destroyed, contamination of the apparatus can be prevented.

Having thus described my invention with the detail and particularity required by the Patent Laws, what is desired protected by Letters Patent is set forth in the following claims.

The invention claimed is:

1. A sample inspection apparatus comprising:
a film having a first surface on which a sample is held such that the first surface is opened to permit access to the sample during primary beam irradiation;
a vacuum chamber for reducing the pressure of an ambient in contact with a second surface of the film;
primary beam irradiation means having an optical axis for irradiating the sample with a primary beam via the film from a side of the second surface of the film;
signal detection means for detecting a secondary signal produced from the sample in response to the irradiation; and
overall control means for controlling operations of the primary beam irradiation means and the signal detection means.

2. A sample inspection apparatus comprising:
a film having a first surface on which a sample is held such that the first surface is open to permit access to the sample during primary beam irradiation;
a vacuum chamber for reducing the pressure of an ambient in contact with a second surface of the film;
primary beam irradiation means connected with the vacuum chamber and irradiating the sample with a primary beam via the film;
signal detection means for detecting a secondary signal produced from the sample in response to the irradiation;
optical image acquisition means having an optical axis for acquiring an optical image of the sample; and
overall control means for controlling operations of the primary beam irradiation means, the signal detection means, and the optical image acquisition means.

3. A sample inspection apparatus as set forth in claim 1 or 2, further including a manipulator having a tip capable of being brought close to or into contact with said sample, and wherein said overall control means controls operation of the manipulator.

4. A sample inspection apparatus as set forth in claim 1 or 2, further including a pressure-adjusting chamber for adjusting the pressure of an ambient in contact with the first surface of said film such that the pressure can be lowered.

5. A sample inspection apparatus as set forth in claim 1 or 2, wherein the first surface of said film is the upper surface of the film, while the second surface of the film is the lower surface of the film.

6. A sample inspection apparatus as set forth in claim 1 or 2, further including an open-close valve that partitions off a space between said film and said primary beam irradiation means in said vacuum chamber.

7. A sample inspection apparatus as set forth in claim 6, further including cleaning means for cleaning the space between the open-close valve and the film in the vacuum chamber.

8. A sample inspection apparatus as set forth in claim 3, wherein there is further provided measurement means for measuring the position of said film or an electrical or physical value between the tip of said manipulator and the film, and wherein said control means avoids contact of the tip of the manipulator with the film, limits operation of the manipulator when the tip is in contact with the film, issues a warning, or closes said open-close valve based on results of the measurement performed by the measurement means.

9. A sample inspection apparatus as set forth in claim 8, wherein said measurement means for measuring the position of said film is formed by said optical image acquisition means.

10. A sample inspection apparatus as set forth in claim 2, wherein said primary beam irradiation means and said optical image acquisition means are disposed opposite to each other with said film interposed therebetween.

11. A sample inspection apparatus as set forth in claim 2, wherein said control means determines a region irradiated with the primary beam emanating from said primary beam irradiation means based on a field of view of said optical image acquisition means, whereby the region corresponding to the field of view is irradiated with the primary beam.

12. A sample inspection apparatus as set forth in claim 2, wherein the optical axis of said primary beam irradiation means is aligned with the optical axis of said optical image acquisition means within a tolerance range of less than 50 μm or the center of the region irradiated with the primary beam emanating from said primary beam irradiation means is aligned with the center of an optical image obtained by said optical image acquisition means within a tolerance range of less than 50 μm.

13. A sample inspection apparatus as set forth in claim 1 or 2, further including film-driving means for moving said film.

14. A sample inspection apparatus as set forth in claim 1 or 2, wherein said film is detachably supported in said vacuum chamber.

15. A sample inspection apparatus as set forth in claim 3, wherein said manipulator performs at least one of an operation for making contact with the sample, an operation for suction, an operation for supplying liquid into the sample or discharging the liquid from it, an operation for supplying electricity to the sample, and an operation for detecting an electrical current flowing out of the sample.

16. A sample inspection apparatus as set forth in claim 1 or 2, wherein said film includes at least one kind of polymer, polyethylene, polyimide, polypropylene, carbon, silicon oxide, silicon nitride, and boron nitride and has a thickness of 10 to 1,000 nm.

17. A sample inspection apparatus as set forth in claim 1 or 2, wherein said primary beam is an electron beam or ion beam, and wherein said secondary signal is at least one kind of backscattered electrons, secondary electrons, absorption current, cathode luminescence light, and X-rays.

18. A sample inspection method of inspecting a sample using a sample inspection apparatus as set forth in claim 1 or 2.

19. A sample inspection system comprising:
a sample inspection apparatus as set forth in claim 1 or 2; and
information-processing means for making a decision about the sample from information created based on the secondary signal which emanates from the sample and which is detected by the sample inspection apparatus.

20. A sample inspection method comprising the steps of:
holding a sample on a first surface of a film such that the first surface is opened to permit access to the sample during primary beam irradiation;
irradiating the sample with a primary beam via the film from a side of a second surface of the film that is in contact with a reduced-pressure ambient; and
detecting a secondary signal produced from the sample in response to the irradiation, thus obtaining information about the sample.

21. A sample inspection method comprising the steps of:
irradiating a sample with a primary beam from primary beam irradiation means via a film held such that the sample is open to permit access to the sample during primary beam irradiation;
obtaining first information about the sample produced in response to the irradiation;
applying a physical, electrical, or chemical action to the sample;
then irradiating the sample with the primary beam via the film;
obtaining second information about the sample produced in response to the irradiation; and
comparing the first information with the second information.

22. A sample inspection method as set forth in claim 21, wherein the physical, electrical, or chemical action is applied to said sample using a manipulator.

23. A sample inspection method as set forth in claim 22, wherein the position of said film is measured or an electrical or physical value between the tip of said manipulator and the film is measured, and wherein contact of the tip of the manipulator with the film is avoided, operation of the manipulator is limited when the tip is in contact with the film, or a warning is issued based on results of the measurement.

24. A sample inspection method as set forth in claim 22 or 23, wherein when the physical, electrical, or chemical action is applied to said sample or when it is detected based on results of the measurement that a spacing between the tip of the manipulator and the film is less than a given distance, a space between the film and said primary beam irradiation means is partitioned off by an open-close valve.

25. A sample inspection method as set forth in any one of claims 20 to 23, wherein said primary beam is an electron beam or ion beam, and wherein said secondary signal is at least one kind of backscattered electrons, secondary electrons, absorption current, cathode luminescence light, and X-rays.

* * * * *